(12) United States Patent
Nara et al.

(10) Patent No.: US 11,717,158 B2
(45) Date of Patent: Aug. 8, 2023

(54) SLIT LAMP MICROSCOPE CAPABLE OF OBSERVING MEIBOMIAN GLAND

(71) Applicant: Takagi Seiko Co., Ltd., Nakano (JP)

(72) Inventors: Takeshi Nara, Nakano (JP); Yusuke Yabana, Nakano (JP); Masayuki Hidai, Nakano (JP)

(73) Assignee: TAKAGI SEIKO CO., LTD., Nakano (JP)

( * ) Notice: Subject to any disclaimer, the term of this patent is extended or adjusted under 35 U.S.C. 154(b) by 463 days.

(21) Appl. No.: 17/025,705

(22) Filed: Sep. 18, 2020

(65) Prior Publication Data

US 2021/0153739 A1 May 27, 2021

(30) Foreign Application Priority Data

Nov. 27, 2019 (JP) .................................. 2019-214203

(51) Int. Cl.
*A61B 3/135* (2006.01)
*A61B 3/00* (2006.01)
*A61B 5/00* (2006.01)
*A61B 3/14* (2006.01)

(52) U.S. Cl.
CPC ............ *A61B 3/135* (2013.01); *A61B 3/0041* (2013.01); *A61B 3/14* (2013.01); *A61B 5/0035* (2013.01); *A61B 5/0075* (2013.01)

(58) Field of Classification Search
CPC ......... A61B 3/135; A61B 3/0041; A61B 3/14; A61B 5/0035; A61B 5/0075; A61B 3/0008
USPC ........................................................ 351/206
See application file for complete search history.

(56) References Cited

U.S. PATENT DOCUMENTS

| | | | | |
|---|---|---|---|---|
| 5,889,577 | A | * | 3/1999 | Kohayakawa ......... A61B 3/024 351/243 |
| 10,039,449 | B2 | | 8/2018 | Sato et al. |
| 2004/0044333 | A1 | * | 3/2004 | Sugiura ............... A61F 9/00817 606/4 |

(Continued)

FOREIGN PATENT DOCUMENTS

| JP | 2012-45321 A | 3/2012 |
|---|---|---|
| JP | 2012-213575 A | 11/2012 |

(Continued)

OTHER PUBLICATIONS

Japanese Office Action for corresponding Japanese Application No. 2019-214203, dated Apr. 12, 2022, with English translation.

*Primary Examiner* — Mohammed A Hasan
(74) *Attorney, Agent, or Firm* — Birch, Stewart, Kolasch & Birch, LLP

(57) ABSTRACT

A slit lamp microscope of the present invention, which is capable of observing a meibomian gland, comprises: a visible light source for emitting slit light; an infrared light source for emitting infrared light, the infrared light source being disposed on a light path of the slit light emitted from the visible light source; a mirror unit including a reflecting mirror or a prism for reflecting the slit light from the visible light source or the infrared light from the infrared light source to irradiate an eye of a subject; and a switching unit for switching the position of the visible light source and the infrared light source, the switching unit being capable of directing one of the visible light source and the infrared light source toward the light path of the slit light.

7 Claims, 7 Drawing Sheets

(56) References Cited

U.S. PATENT DOCUMENTS

| | | | | |
|---|---|---|---|---|
| 2008/0081996 A1* | 4/2008 | Grenon | ................ | A61B 5/0066 600/443 |
| 2010/0237258 A1* | 9/2010 | Welch | ................. | F41H 13/0087 250/492.1 |
| 2016/0051141 A1* | 2/2016 | Sato | ....................... | A61B 3/135 351/214 |

FOREIGN PATENT DOCUMENTS

| | | | |
|---|---|---|---|
| JP | 2016-209291 A | 12/2016 |
| JP | 6180767 B2 | 8/2017 |

* cited by examiner

SLIT LAMP MICROSCOPE CAPABLE OF OBSERVING MEIBOMIAN GLAND

CROSS-REFERENCE TO RELATED APPLICATIONS

This application is based upon and claims the benefit of priority of prior Japanese Patent Application No. P2019-214203, filed on Nov. 27, 2019, the entire contents of which are incorporated herein by reference.

TECHNICAL FIELD

The present invention relates to a slit lamp microscope capable of observing a meibomian gland in an eye of a subject

BACKGROUND ART

A meibomian gland is one of sebaceous glands for supplying lipid to an eyeball and exists in an inner edge of an eyelid.

To observe a meibomian gland of a subject, it is necessary to evert an eyelid of the subject. Thus, apparatuses capable of observing a meibomian gland without everting an eyelid have been developed.

For example, Patent Literature 1 (Japanese Patent No. 6180767) discloses a slit lamp microscope, in which background illumination is performed by backlight including visible light and infrared light and which uses infrared light to observe and image a meibomian gland.

SUMMARY OF INVENTION

Technical Problem

In the conventional slit lamp microscope, e.g., Patent Literature 1, visible light and infrared light are switched to illuminate background, and slit light is visible light only. When background illumination is switched from visible light to infrared light so as to observe a meibomian gland with infrared light, the visible slit light hinders the observation.

Thus, in Patent Literature 1, the slit light is not outputted when the background illumination is switched to the infrared light.

However, in case that the backlight is switched between visible light and infrared light when observing a meibomian gland, an optical mechanism of the backlight must be complex.

Further, output of the slit light must be prohibited while observing a meibomian gland with using the infrared backlight, so controlling the lights must be complex.

The present invention addresses the above described problems, and an object is to provide a slit lamp microscope which is capable of observing a meibomian gland without using backlight and complexly controlling irradiation of the infrared light and turn-off of the slit light.

Solution to Problem

To achieve the object, the slit lamp microscope of the present invention, which is capable of observing a meibomian gland, comprises:

a visible light source for emitting slit light;

an infrared light source for emitting infrared light, the infrared light being disposed on a light path of the slit light emitted from the visible light source;

a mirror unit including a reflecting mirror or a prism for reflecting the slit light from the visible light source or the infrared light from the infrared light source to irradiate an eye of a subject; and a switching unit for switching the position of the visible light source and the infrared light source, the switching unit being capable of directing one of the visible light source and the infrared light source toward the light path of the slit light.

With this structure, the light for irradiating the eye of the subject can be switched between visible light and infrared light, so that observing the meibomian gland can be performed without using a backlight switching mechanism and a complex control of the lights.

In the slit lamp microscope, the switching unit may include a light source supporting body having a side surface to which the visible light source and the infrared light source are attached, and the light source supporting body may be capable of rotating about a rotational axis line arranged perpendicular to the light path of the slit light so as to direct one of the visible light source and the infrared light source toward the light path of the slit light.

With this structure, the light applied toward the light path of the slit light can be easily and securely switched between the visible light and the infrared light by a simple structure.

In the slit lamp microscope according, two electric power supply lines for supplying electric power to the visible light source and the infrared light source may be provided, front end parts of the two electric power supply lines may act as a supplying-positive electrode and a supplying-negative electrode, the light source supporting body may include a visible light source-positive electrode and a visible light source-negative electrode for supplying electric power to the visible light source, and an infrared light source-positive electrode and an infrared light source-negative electrode for supplying electric power to the infrared light source, when the visible light source is located on the light path of the slit light according to the rotational position of the light source supporting body, the supplying-positive electrode may contact the visible light source-positive electrode, the supplying-negative electrode may contact the visible light source-negative electrode, and the infrared light source-positive electrode and the infrared light source-negative electrode may be prohibited from contacting the supplying-positive electrode and the supplying-negative electrode, and when the infrared light source is located on the light path of the slit light according to the rotational position of the light source supporting body, the supplying-positive electrode may contact the infrared light source-positive electrode, the supplying-negative electrode may contact the infrared light source-negative electrode, and the visible light source-positive electrode and the visible light source-negative electrode may be prohibited from contacting the supplying-positive electrode and the supplying-negative electrode.

With this structure, no electric power can be supplied to the light source not directed toward the light path of the slit light. Therefore, wasteful electric power can be eliminated, and electric power consumption can be reduced.

In the slit lamp microscope, the supplying-positive electrode and the supplying-negative electrode may be biased toward the visible light source-positive electrode, the visible light source-negative electrode, the infrared light source-positive electrode and the infrared light source-negative electrode, and the visible light source-positive electrode, the visible light source-negative electrode, the infrared light source-positive electrode and the infrared light source-negative electrode may be biased toward the supplying-positive electrode and the supplying-negative electrode.

With this structure, contact failures between the supplying electrodes and the visible light- and the infrared light source-electrodes can be prevented, and the visible light source and the infrared light source can be securely turned on.

In the slit lamp microscope, the light path of the slit light may be extended in the vertical direction, the light source supporting body may be a cylindrical column or a polygonal column extended in the horizontal direction, the cylindrical column or the polygonal column may be capable of rotating about an axial line, the supplying-positive electrode and the supplying-negative electrode may be arranged such that their front ends are directed, along the horizontal direction, toward the light source supporting body, the visible light source and the infrared light source may be provided in the side surface of the light source supporting body and separated, at a rotational angle of 90° in the rotational direction of the light source supporting body, from each other, when the visible light source is directed toward the light path of the slit light, the visible light source-positive electrode and the visible light source-negative electrode of the visible light source may be located to be directed in the horizontal direction so as to contact the supplying-positive electrode and the supplying-negative electrode, and when the infrared light source is directed toward the light path of the slit light, the infrared light source-positive electrode and the infrared light source-negative electrode of the infrared light source may be located to be directed in the horizontal direction so as to contact the supplying-positive electrode and the supplying-negative electrode.

In the slit lamp microscope, a positioning member, which positions the visible light source when the visible light source is directed toward the light path of the slit light and which positions the infrared light source when the infrared light source is directed toward the light path of the slit light, may be provided to the light source supporting body.

With this structure, the visible light source or the infrared light source can be securely positioned at the position where the visible light source or the infrared light source is directed toward the light path of the slit light.

In the slit lamp microscope, a rotary knob, which can be manually rotated by an observer so as to rotate the light source supporting body about the rotational axis line, may be provided to an end of the light source supporting body.

With this simple structure, the light directed toward the light path of the slit light can be manually easily switched between the visible light and the infrared light by the observer.

The slit lamp microscope may further comprise:
a backlight source for emitting visible light;
a visible light camera for imaging the eye of the subject when the eye of the subject is irradiated by the backlight;
an infrared light camera for imaging the eye of the subject when the eye of the subject is irradiated by infrared light through the light path of the slit light;
a monitor for displaying captured images of the visible light camera and the infrared light camera; and a control unit for simultaneously displaying the captured images of the visible camera and the infrared camera on the monitor.

With this structure, the image of the eye of the subject irradiated by the visible light and the image thereof irradiated by the infrared light can be displayed on a same screen, so that diagnosis can be performed with comparing the both images.

Advantageous Effects of Invention

By employing the slit lamp microscope of the present invention, observing a meibomian gland can be performed without using backlight and complexly controlling irradiation of the infrared light and turn-off of the slit light.

DESCRIPTION OF EMBODIMENTS

Figure 1:
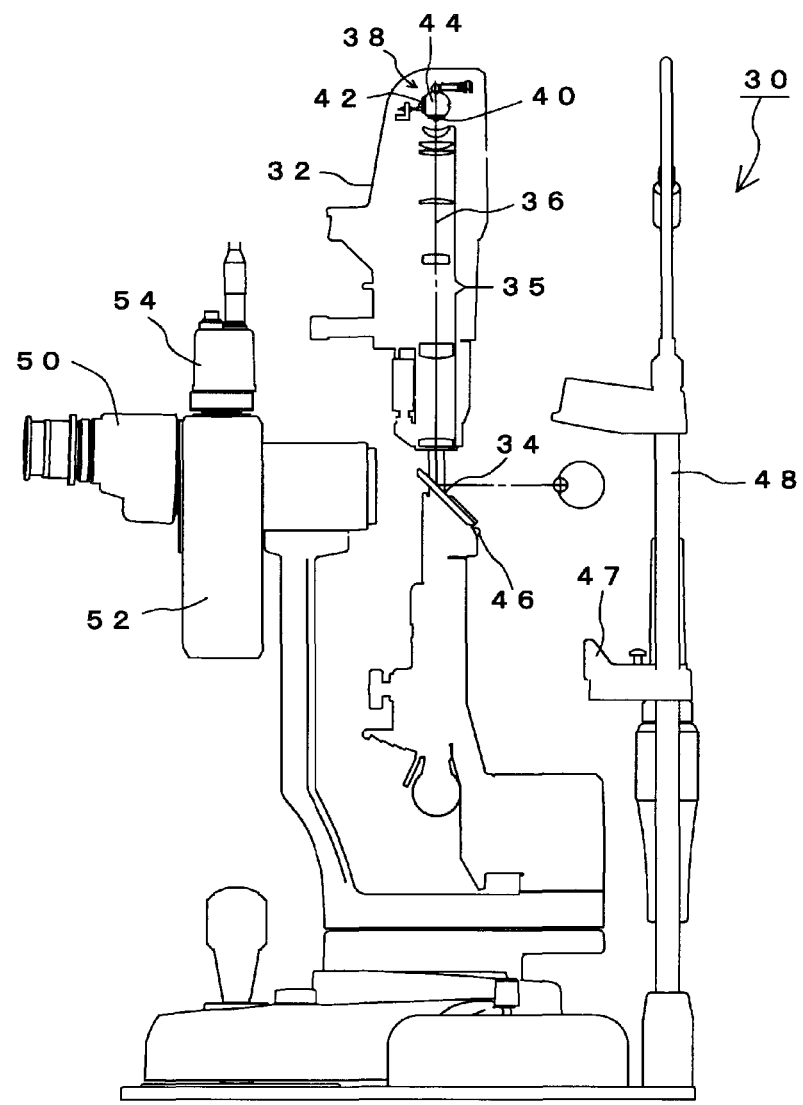
FIG. 1 is a side view showing an overall structure of a slit lamp microscope of an embodiment of the present invention, which is capable of observing a meibomian gland.
Figure 2:
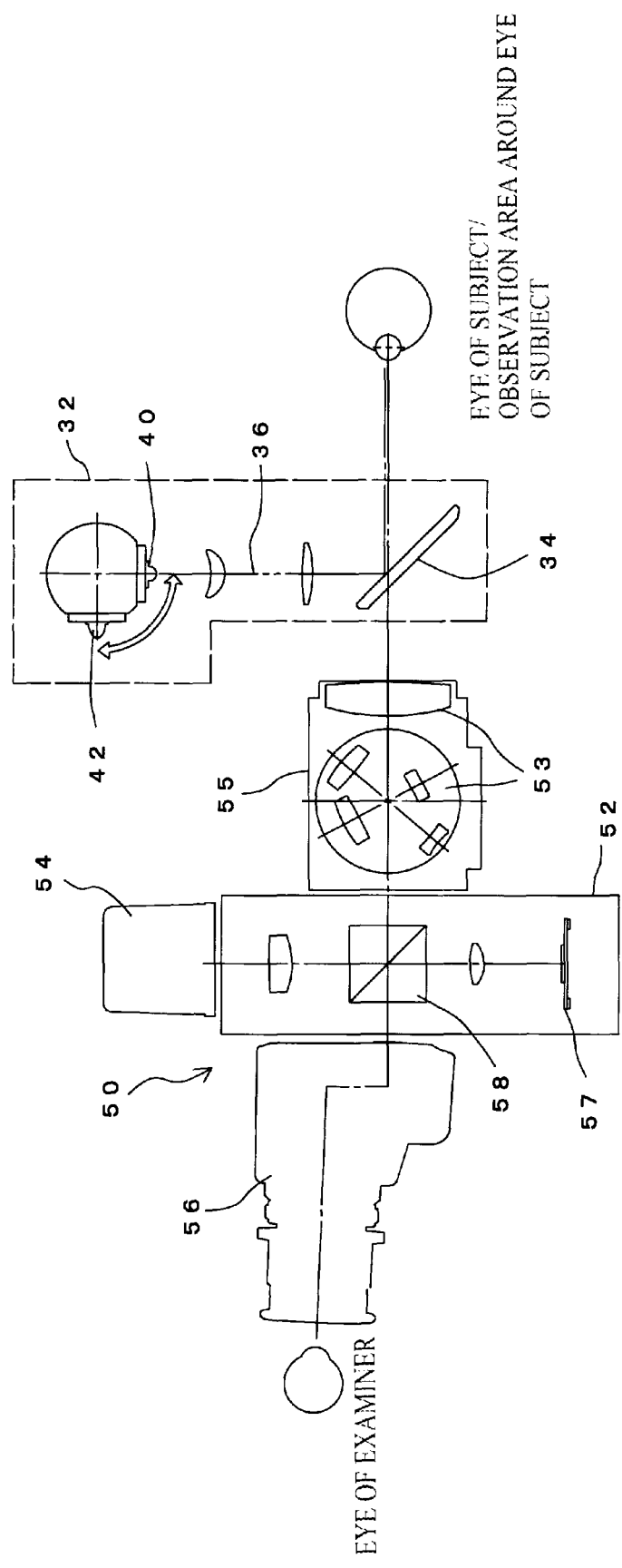
FIG. 2 is an explanation view showing an inner structure of the slit lamp microscope capable of observing a meibomian gland.

An overall structure of a slit lamp microscope relating to the present embodiment, which is capable of observing a meibomian gland, is shown in FIGS. 1 and 2.

The slit lamp microscope 30 comprises: a slit light irradiating section 32, which irradiates visible slit light; and a mirror unit 34 for reflecting the slit light from the slit light irradiating section 32 toward an eye of a subject.

A backlight source 46 for irradiating backlight is provided near the mirror unit 34. In the present embodiment, the backlight source 46 is an LED capable of emitting visible light.

A light path 36 of the slit light, along which a group of optical lenses 35 are arranged, is vertically formed in the slit light irradiating section 32. A slit is provided to the group of optical lenses 35 so as to form the slit light.

The mirror unit 34 is located under the light path 36 of the slit light. The mirror unit 34 reflects light outputted from a light source so as to irradiate the eye of the subject.

A light source section 38 is provided to an upper part of the light path 36 of the slit light. The light source section 38 includes a visible light source 40 for emitting visible light and an infrared light source 42 for emitting infrared light.

Concretely, the visible light source 40 is an LED for emitting visible light, and the infrared light source 42 is an LED for emitting infrared light.

In the light source section 38, the irradiation light source is switched between the visible light source 40 and the infrared light source 42, and any one of the visible light source and the infrared light source is selectively directed toward the light path 36 of the slit light. Switching the irradiation light source is manually performed through a switching unit 44.

Note that, in the present embodiment, the switching unit 44 is manually operated by an observer, but the switching action may be performed by other means, e.g., motor, solenoid.

The slit lamp microscope 30 has a jaw receiving section 47, on which a jaw of the subject can be mounted. The jaw receiving section 47 is provided between two supporting arms 48 which are extended in the vertical direction.

A microscope 50 for observing the eye of the subject whose jaw has been mounted on the jaw receiving section 47 is located to face the jaw receiving section 47.

The microscope 50 comprises: a microscope section 55 including an object lens 53; an eyepiece section 56 including an eyepiece lens; and a camera unit 52 being provided between the microscope section 55 and the eyepiece section 56.

A beam splitter 58 and an image sensor 57 are provided in the camera unit 52. A light beam is split by the beam splitter 58 and inputted to the eyepiece section 56 and the image sensor 57, so that both of direct observation and capturing image data can be performed.

An external camera 54, which is separated from the image sensor 57, can be connected to the camera unit 52.

The external camera 54 is located at a position where a light beam split by another beam splitter can be inputted to the external camera 54.

Preferably, one of the image sensor 57 and the external camera 54 is used for capturing a visible image, and the other is used for capturing an infrared image. Visible light and infrared light are separated by, for example, a filter provided in the microscope section 55.

Figure 3:
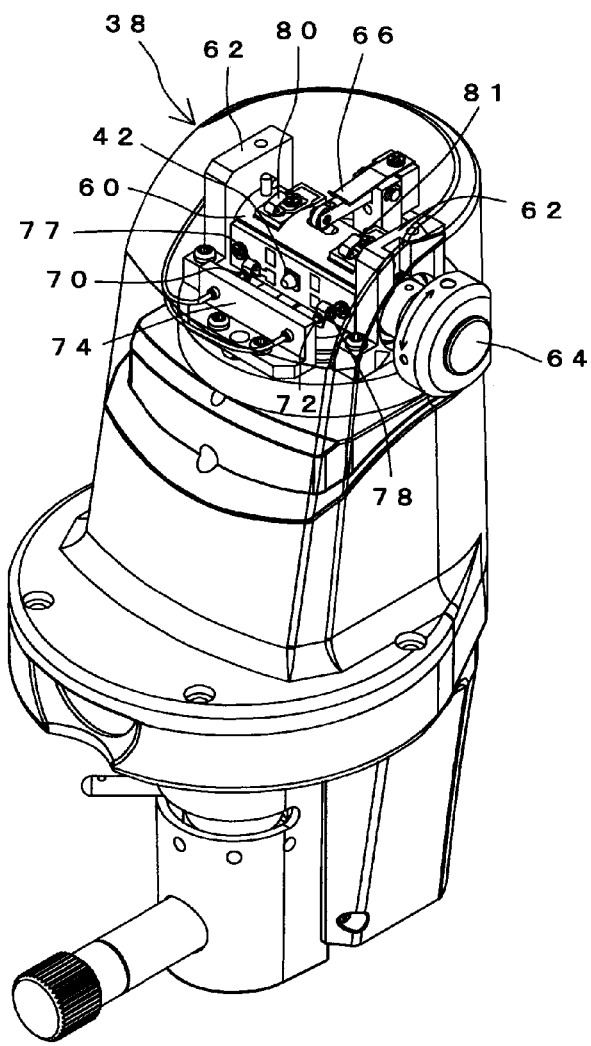
FIG. 3 is a perspective view of a light source section.
Figure 4:
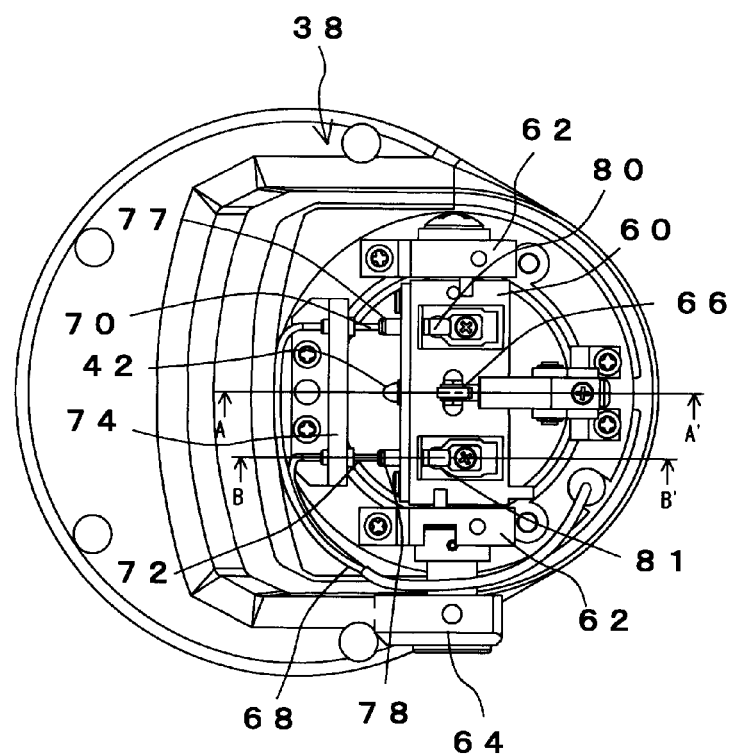
FIG. 4 is a plan view of the light source section.
Figure 5:
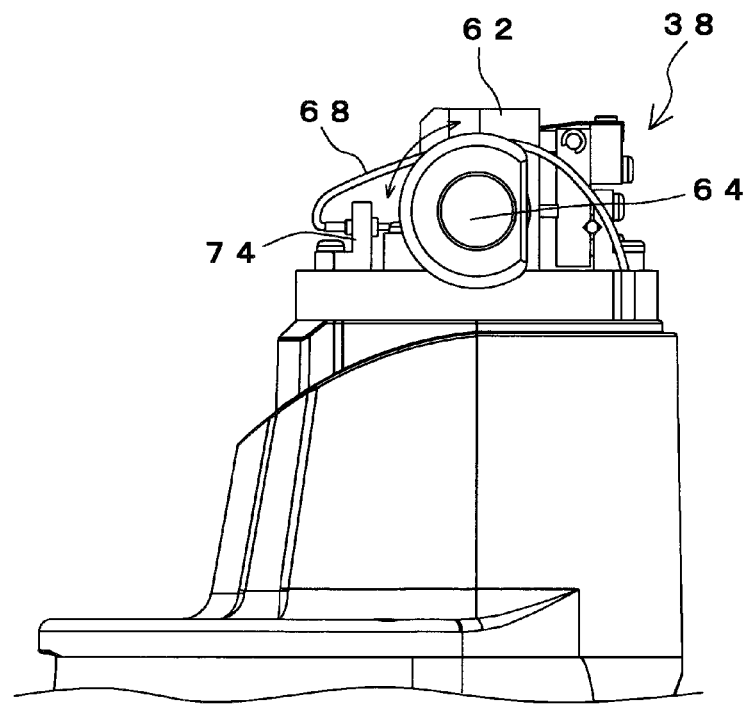
FIG. 5 is a side view of the light source section.

FIG. 3 is a perspective view of the light source section 38, FIG. 4 is a plan view of the light source section 38, and FIG. 5 is a side view of the light source section 38.

Figure 6:
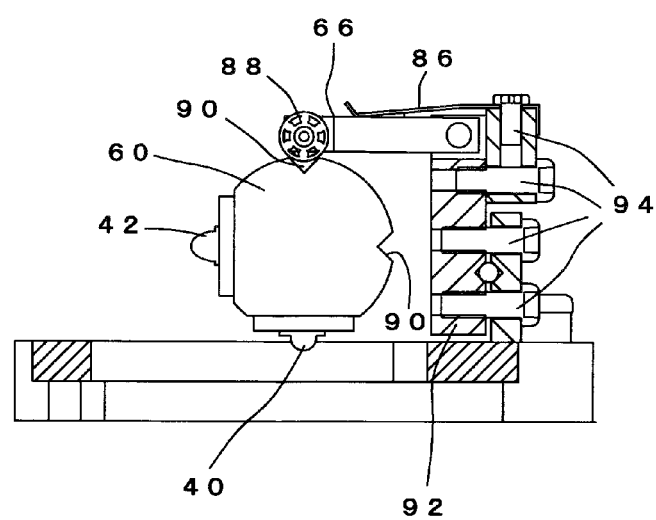
FIG. 6 is a sectional view taken along a line A-A' shown in FIG. 4.
Figure 7:
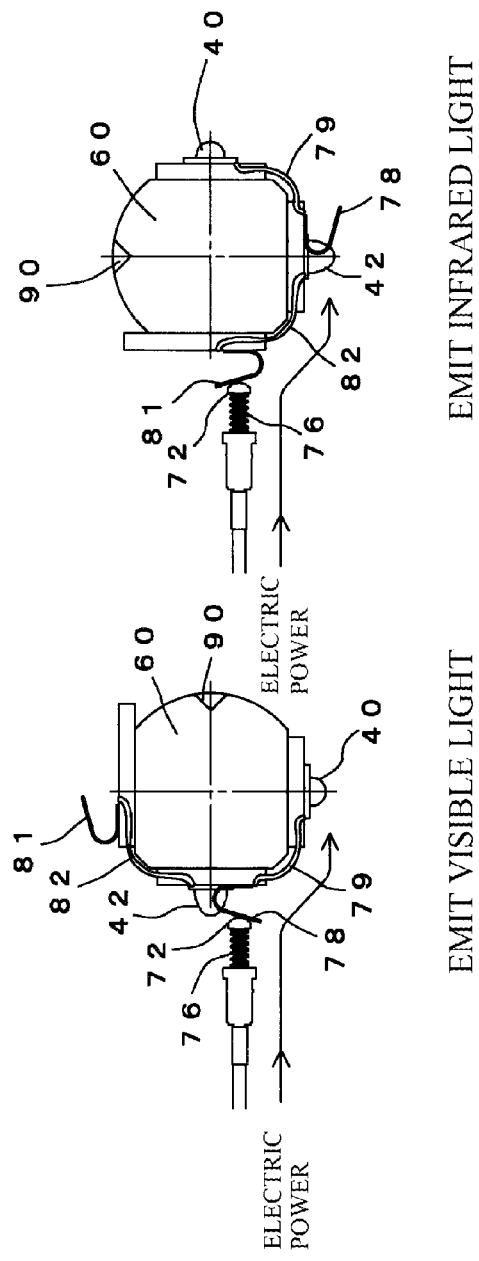
FIG. 7 is a sectional view taken along a line B-B' shown in FIG. 4.

FIG. 6 is a sectional view taken along a line A-A' shown in FIG. 4, and FIG. 7 is a sectional view taken along a line B-B' shown in FIG. 4.

The light source section 38 is provided to an upper part of the slit light irradiating section 32.

The switching unit 44 of the light source section 38 has a light source supporting body 60 to which the visible light source 40 and the infrared light source 42 are attached. The light source supporting body 60 is a cylindrical columnar member whose rotational axis line is directed in the horizontal direction. Both horizontal end parts of the light source supporting body 60 are rotatably held by bearings 62, so that the light source supporting body 60 can be rotated about the horizontal rotational axis line.

A knob 64, which can be manually operated by the observer, is provided to one of the ends of the light source supporting body 60. By manually operating the knob, the light source supporting body 60 is rotated about the horizontal rotational axis line, so that any one of the visible light source 40 and the infrared light source 42 is selectively directed toward the light path 36 (downward) as the irradiation light source.

In case of mechanically switching the light sources 40 and 42, an actuator, e.g., motor, solenoid, may be connected to one of the ends of the light source supporting body 60 instead of the knob 64 so as to rotate the light source supporting body 60 about the horizontal rotational axis line.

The actuator, e.g., motor, solenoid, may be actuated by operating a switch, which is provided to a position easy to manually operate, or the actuator, e.g., motor, solenoid, may be linked with a switch of an infrared image camera described later.

A positioning member 66, which positions the visible light source 40 when the visible light source 40 is directed toward the light path 36 of the slit light and which positions the infrared light source 42 when the infrared light source 42 is directed toward the light path 36 of the slit light, is provided in an upper surface of the light source supporting body 60.

A concrete structure of the positioning member 66 will be described later.

Two electric power supplying lines 68 (one of the two is positive-side line, and the other is negative-side line) for supplying electric power to the visible light source 40 and the infrared light source 42 are provided to the light source section 38. One of front ends of the two electric power supplying lines 68 acts as a supplying-positive electrode 70, and the other acts as a supplying-negative electrode 72. The electric power supplying lines 68 are extended from an electric power source (not shown), which is provided in a lower part of the slit lamp microscope, to the light source section 38.

The supplying-positive electrode 70 and the supplying-negative electrode 72 are attached to an attachment plate 74, directed in the horizontal direction so as to face the light source supporting body 60, and fixed in the light source section 38 with a prescribed separation.

Further, the supplying-positive electrode 70 and the supplying-negative electrode 72 are biased toward front ends by springs 76.

In FIGS. 3-4 and 7 (left side), the light source supporting body 60 is arranged such that the visible light source 40 is directed toward the light path 36 (downward). In FIGS. 3-4 and 7 (left side), the infrared light source 42 is directed in the horizontal direction and arranged such that the infrared light source 42 is arranged to face the supplying-positive electrode 70 and the supplying-negative electrode 72.

Therefore, a visible light source-positive electrode 77 and a visible light source-negative electrode 78, which are used for supplying electric power to the visible light source 40, are provided on both sides of the infrared light source 42, and respectively contact the supplying-positive electrode 70 and the supplying-negative electrode 72.

In the light source supporting section 60, the visible light source-positive electrode 77 and the visible light source-negative electrode 78 are arranged to shift at an angle of 90° with respect to the visible light source 40, so the visible light source-positive electrode 77 and the visible light source-negative electrode 78 are connected to the visible light source 40 by electric wires 79.

In case that the infrared light source 42 is directed toward the light path 36 (downward), an infrared light source-positive electrode 80 and an infrared light source-negative electrode 81, which are used for supplying electric power to the infrared light source 42, are arranged to face the supplying-positive electrode 70 and the supplying-negative electrode 72.

Namely, as shown in FIG. 7 (right side), in the light source supporting section 60, the infrared light source-positive electrode 80 and the infrared light source-negative electrode 81 are oppositely arranged and shifted at an angle of 180° with respect to the visible light source 40.

The infrared light source-positive electrode 80 and the infrared light source-negative electrode 81, which are used for supplying electric power to the infrared light source 42, respectively contact the supplying-positive electrode 70 and the supplying-negative electrode 72.

In the light source supporting section 60, the infrared light source-positive electrode 80 and the infrared light source-negative electrode 81 are arranged to shift at an angle of 90° with respect to the infrared light source 42, so the infrared light source-positive electrode 80 and the infrared light source-negative electrode 81 are connected to the infrared light source 42 by electric wires 82.

Note that, the visible light source-positive electrode 77, the visible light source-negative electrode 78, the infrared light source-positive electrode 80 and the infrared light source-negative electrode 81 are respectively constituted by leaf springs.

The supplying-positive electrode 70 and the supplying-negative electrode 72 are biased toward the front ends by the springs 76. Further, the visible light source-positive electrode 77, the visible light source-negative electrode 78, the infrared light source-positive electrode 80 and the infrared light source-negative electrode 81 are biased toward the supplying-positive electrode 70 and the supplying-negative electrode 72 to contact each other, so that contact failures between the electrodes can be prevented.

In each of the visible light source-positive electrode 77, the visible light source-negative electrode 78, the infrared light source-positive electrode 80 and the infrared light source-negative electrode 81 respectively constituted by the leaf spring, an inlet-side of the leaf spring, from which the supplying-positive electrode 70 and the supplying-negative electrode 72 can enter, is formed as a closed-side, so that the electrodes can be smoothly connected and disconnected when switching the irradiation light between the visible light and the infrared light.

As described above, even if the light source is switched between the visible light source 40 and the infrared light source 42, the same electric power source can be used. An electric power source need not be prepared for each of the light sources, so that production cost can be reduced.

Successively, the positioning member 66 will be explained.

The positioning member 66 is located above the light source supporting body 60 and always biased downward, by a leaf spring 86, so as to contact an upper part of the light source supporting body 60.

The positioning member 66 is fixed to a base section 92 by screws 94. Precise position control can be performed by adjusting the screws 94.

A roller 88 is provided to a front end part of the positioning member 66. Positioning action is performed by fitting the roller 88 into concave parts 90 formed in an outer surface of the light source supporting body 60.

The concave parts 90 are respectively formed at a position, which is oppositely shifted at an angle of 180° with respect to the visible light source 40 and at which the visible light source 40 is directed toward the light path 36 (downward), and at another position, which is oppositely shifted at an angle of 180° with respect to the infrared light source 42 and at which the infrared light source 42 is directed toward the light path 36 (downward).

When the observer manually operates the knob 64 and the roller 88 of the positioning member 66 is fitted into the concave part 90, the observer feels a click feeling and knows that the present position is the position at which the visible light source 40 or the infrared light source 42 is directed toward the light path 36 (downward).

Figure 8:
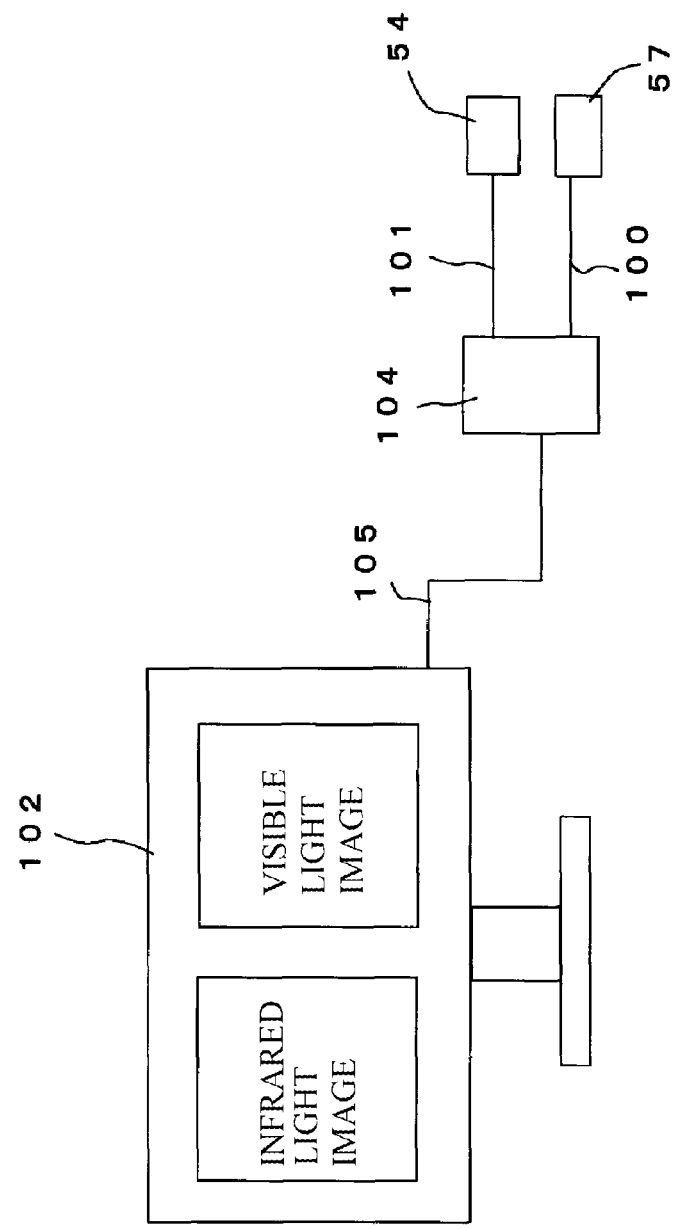
FIG. 8 is an explanation view of an image displaying system.

Next, an image displaying system will be explained with reference to FIG. 8.

As described above, in the present embodiment, the eye of the subject can be imaged by the image sensor 57 in the camera unit 52 and the external camera 54. The image sensor 57 in the camera unit 52 is used for capturing visible light images, and the external camera 54 is used for capturing infrared light images.

In case that the infrared light source 42 of the light source section 38 and the backlight source 46 capable of emitting visible light are turned on, both of the visible light and the infrared light can be emitted toward the eye of the subject.

The image sensor 57 of the camera unit 52 and the external camera 54 are respectively connected to a control unit 104 by image data cables 100 and 101.

The control unit 104 controls to simultaneously display both of visible light image data and infrared light image data on a monitor 102.

An ordinary computer may be used as the control unit 104. Further, a specialized apparatus capable of simultaneously displaying the both image data on one monitor may be used.

The control unit 104 simultaneously inputs the visible light image data and the infrared light image data to the monitor 105 through an image data cable 105 and controls the monitor 102 to simultaneously display the visible light image data and the infrared light image data on the monitor 102.

By simultaneously displaying the visible light image and the infrared light image of the eye of the subject on the same monitor 102, diagnosis of the eye can be correctly and securely performed.

Note that, in the above described embodiment, the light source section 38 is provided above the mirror unit 34, and the visible light or the infrared light is reflected, by the mirror unit 34, toward the eye of the subject.

The mirror unit 34 may be changed to, for example, a prism, and the light source section 38 capable of switching the irradiation light between visible light and infrared light may be provided under the mirror unit 34 or the prism.

What is claimed is:

1. A slit lamp microscope capable of observing a meibomian gland, comprising:
    a visible light source for emitting slit light;
    an infrared light source for emitting infrared light, the infrared light being disposed on a light path of the slit light emitted from the visible light source;
    a mirror unit including a reflecting mirror or a prism for reflecting the slit light from the visible light source or the infrared light from the infrared light source to irradiate an eye of a subject;
    a switching unit for switching the position of the visible light source and the infrared light source, the switching unit being capable of directing one of the visible light source and the infrared light source toward the light path of the slit light;
    wherein the switching unit includes a light source supporting body having a side surface to which the visible light source and the infrared light source are attached, and
    the light source supporting body is capable of rotating about a rotational axis line arranged perpendicular to the light path of the slit light so as to direct one of the visible light source and the infrared light source toward the light path of the slit light.

2. The slit lamp microscope according to claim 1, wherein two electric power supply lines for supplying electric power to the visible light source and the infrared light source are provided, front end parts of the two electric power supply lines act as a supplying-positive electrode and a supplying-negative electrode, the light source supporting body includes a visible light source-positive electrode and a visible light source-negative electrode for supplying electric power to the visible light source, and an infrared light source-positive electrode and an infrared light source-negative electrode for supplying electric power to the infrared light source, when the visible light source is located on the light path of the slit light according to the rotational position of the light source supporting body, the supplying-positive electrode contacts the visible light source-positive electrode, the supplying-negative electrode contacts the visible light source-negative electrode, and the infrared light source-positive electrode and the infrared light source-negative electrode are prohibited from contacting the supplying-positive electrode and the supplying-negative electrode, and when the infrared light source is located on the light path of the slit light according to the rotational position of the light source supporting body, the supplying-positive electrode contacts the infrared light source-positive electrode, the supplying-negative electrode contacts the infrared light source-negative electrode, and the visible light source-positive electrode and the visible light source-negative electrode are prohibited from contacting the supplying-positive electrode and the supplying-negative electrode.

3. The slit lamp microscope according to claim 2, wherein the supplying-positive electrode and the supplying-negative electrode are biased toward the visible light source-positive electrode, the visible light source-negative electrode, the infrared light source-positive electrode and the infrared light source-negative electrode, and the visible light source-positive electrode, the visible light source-negative electrode, the infrared light source-positive electrode and the infrared light source-negative electrode are biased toward the supplying-positive electrode and the supplying-negative electrode.

4. The slit lamp microscope according to claim 2, wherein the light path of the slit light is extended in the vertical direction, the light source supporting body is a cylindrical column or a polygonal column extended in the horizontal direction, the cylindrical column or the polygonal column is capable of rotating about an axial line, the supplying-positive electrode and the supplying-negative electrode are arranged such that their front ends are directed, along the horizontal direction, toward the light source supporting body, the visible light source and the infrared light source are provided in the side surface of the light source supporting body and separated, at a rotational angle of 90° in the rotational direction of the light source supporting body, from each other, when the visible light source is directed toward the light path of the slit light, the visible light source-positive electrode and the visible light source-negative electrode of the visible light source are located to be directed in the horizontal direction so as to contact the supplying-positive electrode and the supplying-negative electrode, and when the infrared light source is directed toward the light path of the slit light, the infrared light source-positive electrode and the infrared light source-negative electrode of the infrared light source are located to be directed in the horizontal direction so as to contact the supplying-positive electrode and the supplying-negative electrode.

5. The slit lamp microscope according to claim 1, wherein a positioning member, which positions the visible light source when the visible light source is directed toward the light path of the slit light and which positions the infrared light source when the infrared light source is directed toward the light path of the slit light, is provided to the light source supporting body.

6. The slit lamp microscope according to claim 1, wherein a rotary knob, which can be manually rotated by an observer so as to rotate the light source supporting body about the rotational axis line, is provided to an end of the light source supporting body.

7. The slit lamp microscope according to claim 1, further comprising:

a backlight source for emitting visible light;

a visible light camera for imaging the eye of the subject when the eye of the subject is irradiated by the backlight;

an infrared light camera for imaging the eye of the subject when the eye of the subject is irradiated by infrared light through the light path of the slit light;

a monitor for displaying captured images of the visible light camera and the infrared light camera; and a control unit for simultaneously displaying the captured images of the visible camera and the infrared camera on the monitor.

* * * * *